US007824708B2

(12) United States Patent
Leverett et al.

(10) Patent No.: US 7,824,708 B2
(45) Date of Patent: *Nov. 2, 2010

(54) LIPOSOME CONTAINING CARDIOLIPIN FOR IMPROVEMENT OF MITOCHONDRIAL FUNCTION

(75) Inventors: Jesse C. Leverett, Rockford, MI (US); Stephen R. Missler, Grand Rapids, MI (US); David J. Fast, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 995 days.

This patent is subject to a terminal disclaimer.

(21) Appl. No.: 11/636,889

(22) Filed: Dec. 11, 2006

(65) Prior Publication Data

US 2008/0138392 A1 Jun. 12, 2008

(51) Int. Cl.
*A61K 9/127* (2006.01)
(52) U.S. Cl. .................................... 424/450
(58) Field of Classification Search ................. 424/450
See application file for complete search history.

(56) References Cited

U.S. PATENT DOCUMENTS

| 5,503,776 | A | 4/1996 | Murase et al. |
| 2002/0048551 | A1 | 4/2002 | Keller et al. |
| 2004/0057974 | A1 | 3/2004 | Sachdev |
| 2004/0081681 | A1 | 4/2004 | Vromen |
| 2005/0008665 | A1 | 1/2005 | Batzer et al. |
| 2005/0181037 | A1 | 8/2005 | Ahmad et al. |
| 2005/0197407 | A1 | 9/2005 | DiNardo et al. |
| 2005/0266068 | A1 | 12/2005 | Ahmad et al. |
| 2005/0277611 | A1 | 12/2005 | Ahmad et al. |
| 2006/0034908 | A1* | 2/2006 | Bhamidipati et al. ........ 424/450 |
| 2006/0216251 | A1 | 9/2006 | Morariu |

FOREIGN PATENT DOCUMENTS

| EP | 0 201 956 A2 | 11/1986 |
| WO | WO 01/49305 A2 | 7/2001 |
| WO | WO 01/49305 A3 | 7/2001 |
| WO | WO 03/099830 A2 | 12/2003 |
| WO | WO 2005/079185 A2 | 9/2005 |
| WO | WO 2006/004935 A2 | 1/2006 |

OTHER PUBLICATIONS

Bergman, Margalit et al., 'The antioxidant activity of aqueous spinach extract: chemical identification of active fractions', *Phytochemistry*, vol. 58, 2001, pp. 143-152.

(Continued)

*Primary Examiner*—Gollamudi S Kishore
(74) *Attorney, Agent, or Firm*—Brinks Hofer Gilson & Lione; G. Peter Nichols

(57) ABSTRACT

Disclosed herein is a composition comprising a liposome, a cardiolipin, and at least one antioxidant, wherein the composition is useful for improving, maintaining, or restoring a mitochondrial membrane and/or mitochondrial function. In one example, the liposome is primarily composed of phosphatidylcholine, the cardiolipin is tetraoleoyl-cardiolipin, and the at least one antioxidant is methylgentisate, l-carnosine, or both. The composition may be topically administered, orally administered, or parenterally administered, for example administered by injection. If topically administered, the composition may be administered for example, as a cream, lotion, gel, paste, spray, tonic, or other suitable form and may contain various additives, for example, one or more of an emollient, a humectant, a penetration enhancer, a vitamin, a fragrance, a pigment, and a moisturizer.

9 Claims, 6 Drawing Sheets

OTHER PUBLICATIONS

Bergman, Margalit et al., 'Scavenging of reactive oxygen species by a novel glucurinated flavonoid antioxidant isolated and purified from spinach', *Phytochemistry*, vol. 62, 2003, pp. 753-762.

Lasic, Dan D., 'Novel applications of liposomes', *Trends in Biotechnology*, vol. 16, No. 7, 1998, pp. 307-321.

Lomnitski, Liat et al., Composition, Efficacy, and Safety of Spinach Extracts, *Nutrition and Cancer*, vol. 46, No. 2, 2003, pp. 222-231.

McMillin, Jeanie B. et al., 'Cardiolipin and apoptosis', *Biochimica et Biophysica Acta*, vol. 1585, 2002, pp. 97-107.

International Search Report for PCT/US2007/023280, dated Mar. 17, 2008, 5 pgs.

International Search Report for PCT/US2007/024617, dated Mar. 28, 2008, 4 pgs.

Notification Concerning Transmittal of International Preliminary Report on Patentability with Written Opinion of the International Search Authority for PCT/US2007/024617, dated Jun. 25, 2009, 9 pp.

Wei, Y.H., et al. "Mitochondrial Theory of Aging Matures-Roles of mtDNA Mutation and Oxidative Stress in Human Aging," Zhonghua Yi Xue Za Zhi (Taipei), 64(5):259-70 (2001).

Mileykovskaya, E., et al., "Cardiolipin in Energy Transducing Membranes," Biochem. (Moscow) 70(2):154-158 (2005).

Gorbenko, G.P., et al., "Cytochrome $c$ Interaction with Cardiolipin/Phosphatidylcholine Model Membranes: Effect of Cardiolipin Protonation," Biophys. J. BioFAST, (Mar. 24, 2006).

Paradies, G., et al., "Reactive Oxygen Species Affect Mitochondrial Electron Transport Complex I Activity Through Oxidative Cardiolipin Damage," Gene, 286:135-141 (2002).

Paradies, G., et al., "Reactive Oxygen Species Generated by the Mitochondrial Respiratory Chain Affect the Complex III Activity Via Cardiolipin Peroxidation in Beef-Heart Submitochondrial Particles," Mitochondrion, 1:151-159 (2001).

Kohen, R., et al., "Antioxidant Activity of Carnosine, Homocarnosine, and Anserine Present in Muscle and Brain," Proc. Natl. Acad. Sci., USA 85:3175-3179 (1988).

The Lipid Library (on-line article), "Diphosphatidylglycerol (Cardiolipin) Structure, Occurrence, Biology and Analysis," updated Feb. 3, 2006 http://www.lipidlibrary.co.uk/lipids/dpg/index.htm.

Petrosillo G., et al., "Role of Reactive Oxygen Species and Cardiolipin in the Release of Cytochrome $c$ from Mitochondria," The FASEB J., 17:2202-2208 (2003).

Kowaltowski, A.J., et al., "Minireview: Mitochondrial Permeability Transition and Oxidative Stress," FEBS Letters 495:12-15 (2001).

Miyoshi, N., et al., "Age-Dependent Cell Death and the Role of ATP in Hydrogen Peroxide-Induced Apoptosis and Necrosis," PNAS, 103(6):1727-1731 (2006).

Bruce, A. "Skeletal Muscle Lipids. III. Changes in Fatty Acid Composition of Individual Phosphoglycerides in Man From Fetal to Middle Age," J. Lipid Res., 15:109-113 (1974).

Shigenaga, M.K., et al., "Oxidative Damage and Mitochondrial Decay in Aging," Proc. Natl. Acad. Sci. USA, 91:10771-10778 (1994).

Greco, M., et al., "Marked Aging-Related Decline in Efficiency of Oxidative Phosphorylation in Human Skin Fibroblasts," The FASEB J. express article 10.1096/fj.02-1009jfe. Published online Jul. 18, 2003.

Hagen, T.M., et al., "Mitochondrial Decay in Aging, Reversal through Supplementation of Acetyl-L-Carnitine and N-tert-Butyl-α-phenyl-nitrone," Ann. N.Y. Acad. Sci., 214-223.

\* cited by examiner

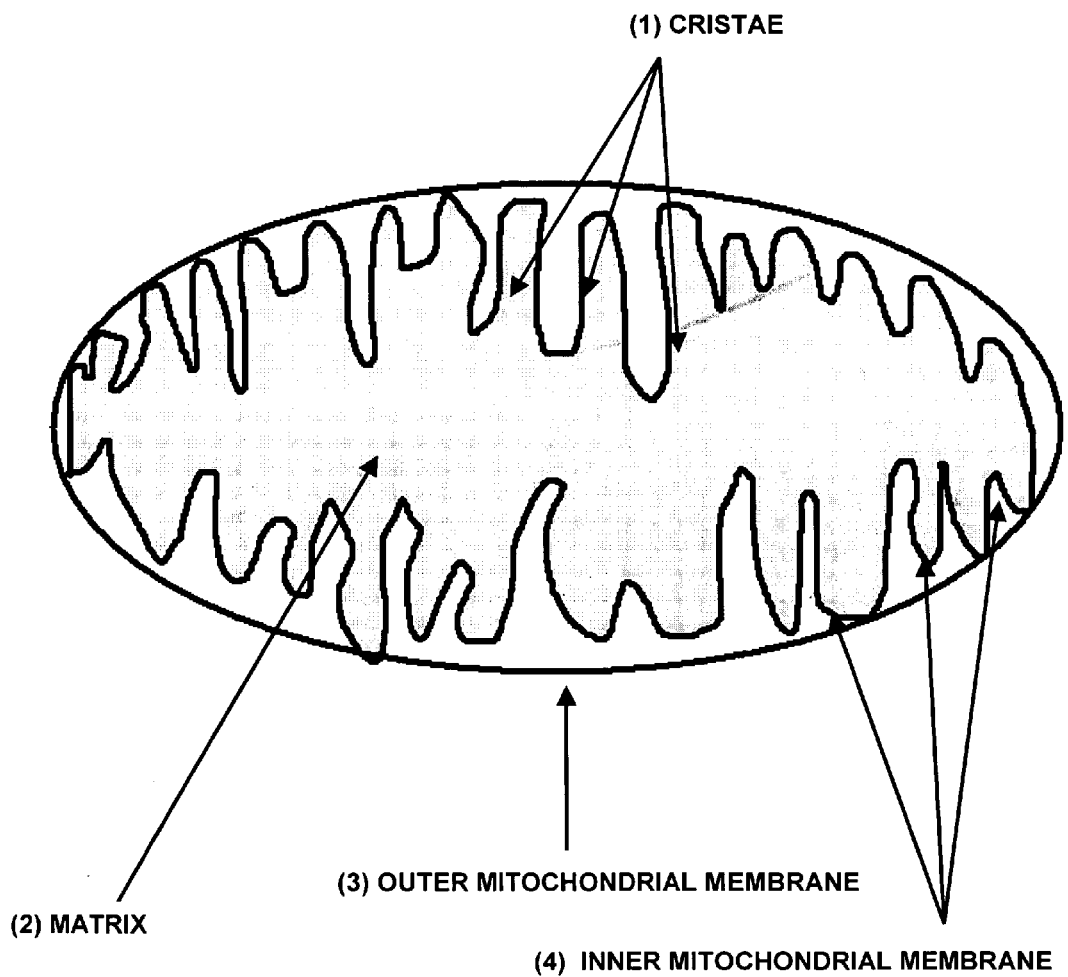
FIGURE 1: MITOCHONDRION

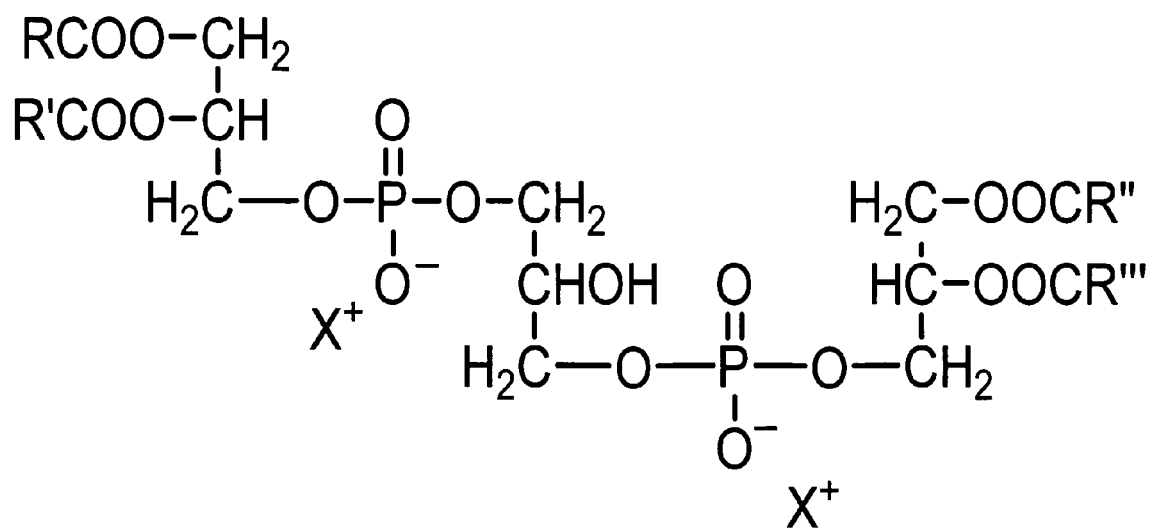
FIGURE 2: CARDIOLIPIN

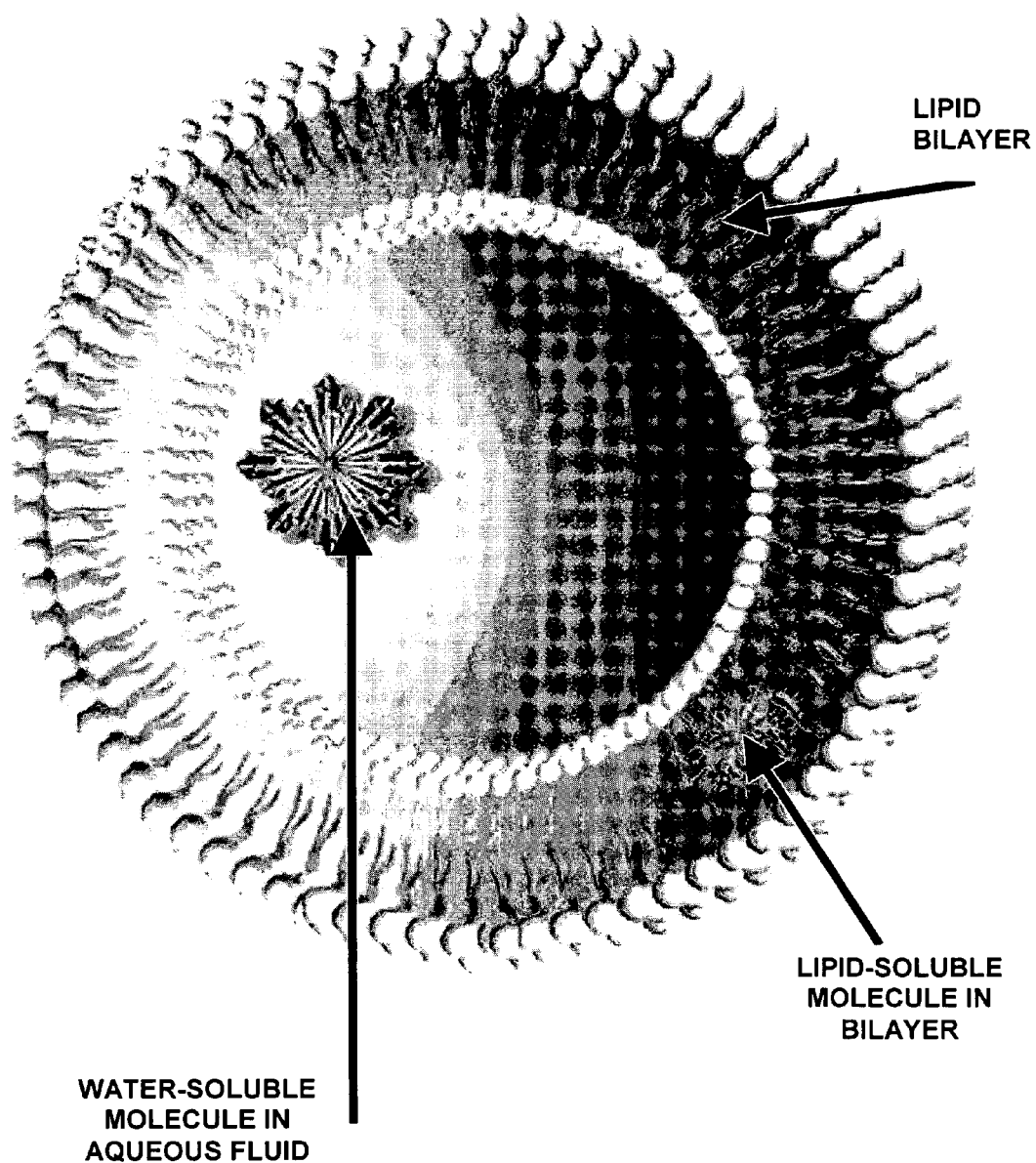
FIGURE 3: LIPOSOME

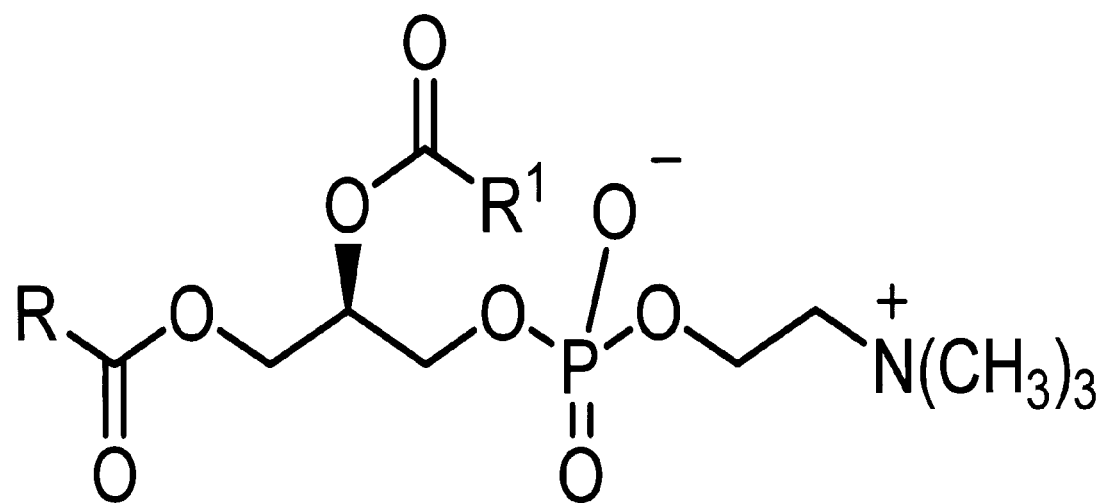
FIGURE 4: PHOSPHATIDYLCHOLINE

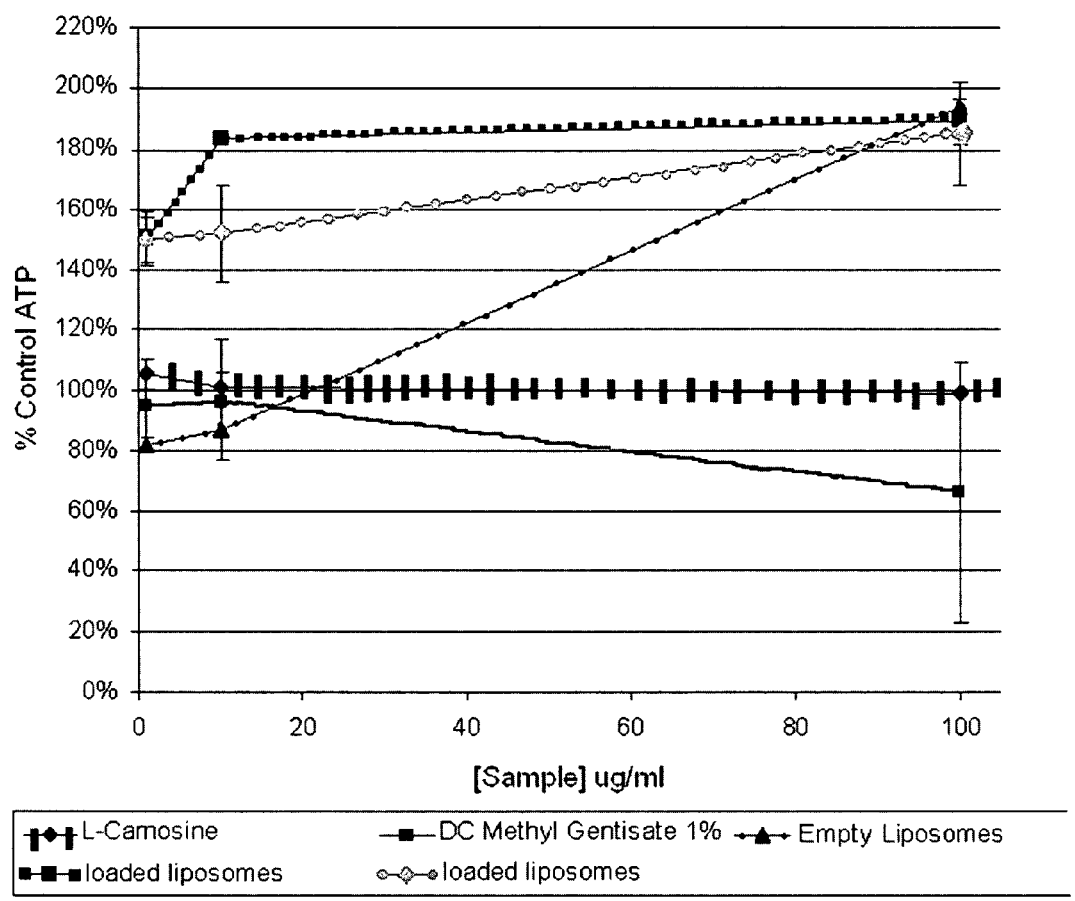
FIGURE 5: CELLULAR ATP PRODUCTION

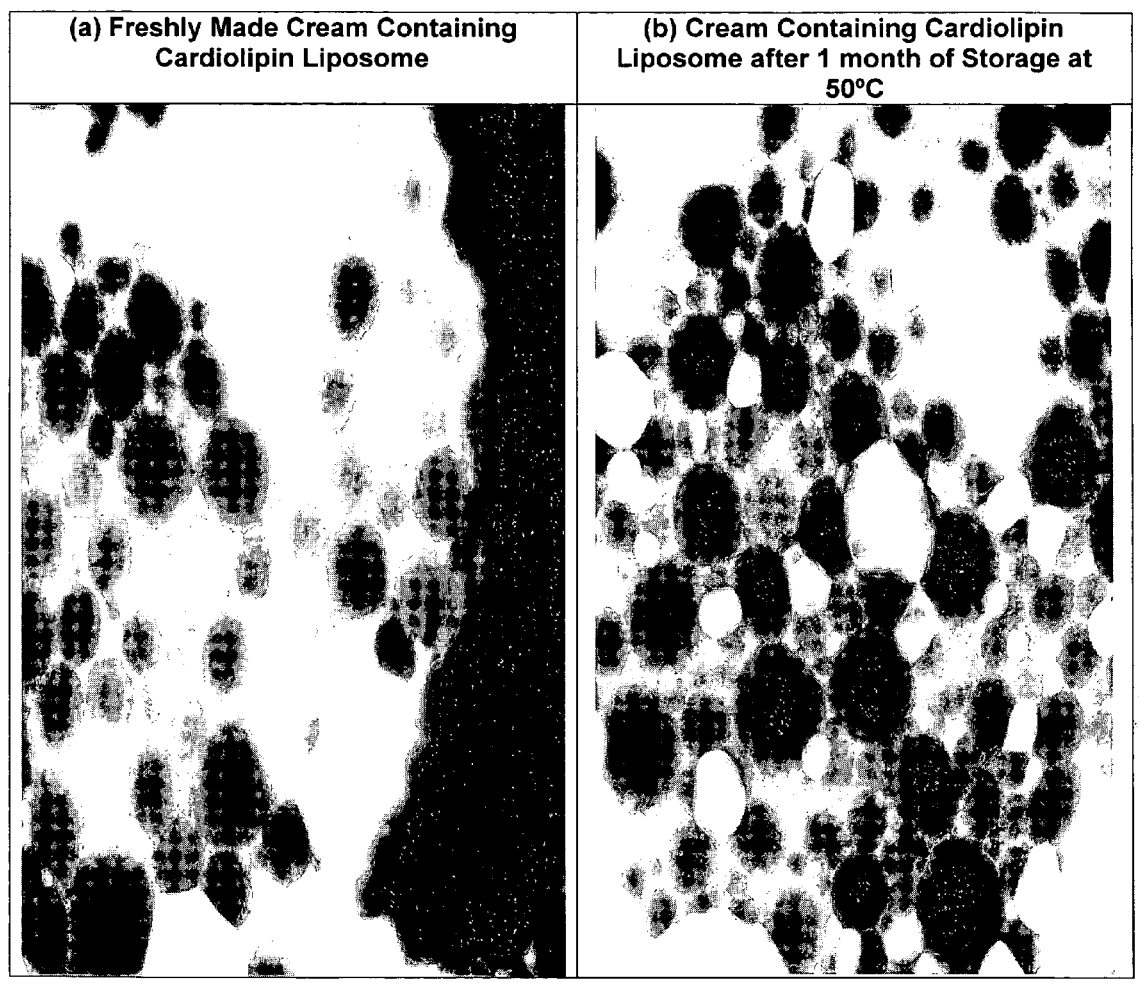
Figure 6: TEM Photographs

LIPOSOME CONTAINING CARDIOLIPIN FOR IMPROVEMENT OF MITOCHONDRIAL FUNCTION

BACKGROUND

Oxygen free radicals or reactive oxygen species (ROS) are highly reactive species which are known to be the major factor in cell injury via oxidation and subsequent function impairment of lipids, proteins, and nucleic acids. Indeed, active oxygen has been suggested as a major cause of aging and several diseases including cancer. ROS in particular are known to damage mitochondria. Oxidative damage to mitochondria is considered to be a major factor in cellular aging and ultimate cell death.

A mitochondrion (singular of mitochondria) is part of every cell in the body that contains genetic material. Indeed, they are found in the cells of all eukaryotes. Mitochondria are responsible for processing oxygen and converting substances from foods into energy essential for cellular functions. Mitochondria produce energy in the form of adenosine triphosphate (ATP), which is then transported to the cytoplasm of a cell for use in numerous cell functions. Mitochondria are known as the powerhouses of the cell because the ATP they produce supplies approximately 90 percent of the metabolic energy used by multi-cellular creatures.

The role of mitochondria in oxygen metabolism makes them prime targets for damage from oxygen radicals. Specifically, the mitochondrial respiratory chain (i.e. the electron transport chain) has been recognized as a major intracellular source of ROS. Formation of ATP in the mitochondria results in release of highly reactive superoxide free radicals, which can transform into other ROS such as hydrogen peroxide and hydroxyl radical. Cells have mechanisms to cope with this oxidative stress, but the efficiency of coping declines with age and the influence of extrinsic factors such as stress. Eventually mitochondria become inefficient in their ability to produce ATP leading to a loss of cellular function and often even cell death.

ROS are capable of causing damage to mitochondria by structural degradation of proteins and lipids within the inner mitochondrial membrane. One of the most damaging ROS species is the hydroxyl radical which causes lipid peroxidation. As lipid peroxidation increases over time, one of the major lipids in the inner mitochondrial membrane, cardiolipin, undergoes structural changes. These structural changes result in damage to the inner membrane and associated cardiolipin-protein interactions, which are critical to electron transport. For example, cytochrome c attaches to cardiolipin in a healthy, normal functioning mitochondrion. However, when cardiolipin is degraded, cytochrome c is released, which in turn triggers the cascade of events leading to programmed cell death.

It has been suggested that exogenous addition of cardiolipin may improve overall mitochondrial dysfunction. However, numerous difficulties have been encountered when attempting to exogenously deliver cardiolipin. Cardiolipin is unstable and extremely susceptible to oxidative degradation. For example, human cardiolipin contains polyunsaturated fatty acids, with over 85% belonging to the linoleic acid series. Unlike saturated or monounsaturated fatty acids, polyunsaturated fatty acids such as linoleic acid are readily degraded by ROS. In addition, simple topical application of cardiolipin would not be expected to penetrate to the inner mitochondrial membrane in a complex fully functional cell based model, and particularly in vivo because of oxidative breakdown of cardiolipin and barriers to transport.

There currently are several other ways to address mitochondrial dysfunction but each is limited in that they do not address the most critical failure associated with mitochondrial aging. For example, one proposed solution has aimed at increasing ATP production by providing nothing more than a substrate for ATP production but this solution completely fails to address overall mitochondrial dysfunction. Another proposed solution for mitochondrial dysfunction is based on exogenous addition of antioxidants. This approach has achieved some level of success by preserving the current state and function of the mitochondria. However, this approach does not address repair of existing damage and therefore is not an ideal solution. Yet another example of a solution is NeoLipid®, specifically the Lipid Conjugate Gemcitabine (cardiolipin conjugate gemcitabine) available from NeoPharm (Waukegan, Ill.). NeoLipid® is a cationically modified cardiolipin embedded in a phosphatidylcholine liposome. However, even this solution is not ideal for a topical treatment aimed at treating mitochondrial dysfunction.

BRIEF SUMMARY

Mitochondrial dysfunction is directly related to oxidative damage, including lipid peroxidation caused by ROS and loss of cardiolipin from the mitochondrial membrane. Mitochondrial dysfunction also is directly associated with cellular aging and death. The present invention is based on a unique composition that not only maintains mitochondrial function but that also improves and restores mitochondrial function and/or repairs mitochondrial membranes. Specifically, the compositions of the present invention are unique combinations of cardiolipin-embedded liposomes and antioxidants.

In one example, a composition of the present invention is a cardiolipin and antioxidant embedded liposome.

In a further example, a composition of the present invention is a liposome, for example a liposome primarily composed of phosphatidylcholine (or phosphatidyl choline), embedded with cardiolipin, wherein the cardiolipin is one of tetraoleoyl-cardiolipin, tetrapalmitoleoyl-cardiolipin, or tetramyristoyl-cardiolipin and is embedded in the phospholipid bilayer of the liposome; and one or more antioxidants, wherein the one or more antioxidants are embedded in the phospholipid bilayer of the liposome, the aqueous center of the liposome, or both. In one example, at least one antioxidant may be a water soluble antioxidant. In another example, at least one antioxidant may be a lipid soluble antioxidant. In a further example, at least one antioxidant may be a singlet-oxygen scavenger. In a further example, an antioxidant included in the composition of the present invention may be either both water soluble and a singlet-oxygen scavenger or lipid soluble and a singlet-oxygen scavenger.

In another example, a composition of the present invention is a liposome primarily composed of phosphatidylcholine, embedded with cardiolipin, for example tetraoleoyl-cardiolipin, and at least one antioxidant, for example one or more of methylgentisate (or methyl gentisate) and l-carnosine.

In another example, a composition of the present invention is a liposome, for example a liposome primarily composed primarily of phosphatidylcholine, embedded with a cardiolipin derived from a seed oil and at least one antioxidant. In a further example, the at least one antioxidant may be methylgentisate, l-carnosine, butylated hydroxytoluene (BHT), tert-butylhydroquinone (TBHQ), or some combination thereof.

In a further example, a composition of the present invention may include one or more of lipids, phospholipids, penetration enhancers, moisturizers, fragrances, ceramides, sphingolipids, proteins, cholesterol, phytosterols, cholesterol sulfate, sugars, vitamins, minerals, or any other compounds naturally found in a cell membrane.

In one example, the composition of the present invention is topically administered as a cream, lotion, gel, tonic, oil-in-water emulsion, water-in-oil emulsion, paste, or spray. In other examples, the composition of the present invention may be orally administered or parenterally, for example, administered by injection.

In a further example, the compositions of the present invention are stable and not susceptible to substantial oxidative damage when stored at room temperature, approximately 68° F./21.1° C. for any period of time ranging from at least an hour to a day, to several days, to a week, to several weeks, to a month, to several months, to a year, to several years.

In another example, the compositions of the present invention are stable and not susceptible to substantial oxidative damage when stored at temperatures ranging from approximately 10° C. to approximately 60° C., desirably from approximately 20° C. to approximately 55° C., desirably from approximately 30° C. to approximately 50° C.

In a further example, the present invention is a method of improving, restoring, or maintaining mitochondrial function comprising topically administering a composition comprising a liposome embedded with cardiolipin and antioxidants. In one example, the liposome is primarily composed of phosphatidylcholine and embedded with cardiolipin, wherein the cardiolipin is, for example, one of tetrapalmitoleoyl-cardiolipin, tetramyristoyl-cardiolipin, or tetraoleoyl-cardiolipin and is embedded in the phospholipid bilayer of the liposome; and one or more antioxidants, wherein the one or more antioxidants are embedded in the phospholipid bilayer of the liposome, the aqueous center of the liposome, or both. In one example, at least one antioxidant may be a water soluble antioxidant. In another example, at least one antioxidant may be a lipid soluble antioxidant. In a further example, at least one antioxidant may be a singlet-oxygen scavenger. In a further example, an antioxidant included in the composition of the present invention may be either both water soluble and a singlet-oxygen scavenger or lipid soluble and a singlet-oxygen scavenger. In yet a further example, the antioxidant in embedded in the liposome may be methylgentisate, l-carnosine, or both.

In another example, the present invention is a method of repairing a mitochondrial membrane comprising topically administering a composition comprising a liposome embedded with cardiolipin and antioxidants. In one example, the liposome is primarily composed of phosphatidylcholine and embedded with cardiolipin, wherein the cardiolipin is preferably one of tetrapalmitoleoyl-cardiolipin, tetramyristoyl-cardiolipin, or tetraoleoyl-cardiolipin and is embedded in the phospholipid bilayer of the liposome; and one or more antioxidants, wherein the one or more antioxidants are embedded in the phospholipid bilayer of the liposome, the aqueous center of the liposome, or both. In one example, at least one antioxidant may be a water soluble antioxidant. In another example, at least one antioxidant may be a lipid soluble antioxidant. In a further example, at least one antioxidant may be a singlet-oxygen scavenger. In a further example, an antioxidant included in the composition of the present invention may be either both water soluble and a singlet-oxygen scavenger or lipid soluble and a singlet-oxygen scavenger. In yet a further example, the antioxidant in embedded in the liposome may be methylgentisate, l-carnosine, or both.

BRIEF DESCRIPTION OF THE DRAWINGS

FIG. 1 is an illustration of a mitochondrion showing its (1) cristae, (2) matrix, (3) outer membrane, and (4) inner membrane.

FIG. 2 is a diagram of the chemical structure of cardiolipin.

FIG. 3 is an illustration of a liposome showing its lipid bilayer (1) including the hydrophilic heads of the lipids (2); the hydrophobic tails of the lipids (3); the aqueous center (4); and the space between the hydrophobic tails (5).

FIG. 4 is a diagram of the chemical structure of phosphatidylcholine.

FIG. 5 is a graph illustrating ATP production achieved using (a) l-carnosine; (b) DC methylgentisate 1%; (c) empty liposome (cardiolipin only); (d) loaded liposome (i.e. liposome loaded with l-carnosine, methylgentisate, and cardiolipin); and (e) loaded liposome (i.e. liposome loaded with l-carnosine, methylgentisate, and cardiolipin).

FIG. 6 is a comparison of two TEM pictures (photographs) taken using a Zeiss-902 electron microscope with ESI. FIG. 6(a) is TEM picture (photograph) of a standard cream formulation containing a liposome embedded with cardiolipin, methylgentisate, and l-carnosine. The TEM picture (photograph) in 6(a) was taken soon after the cream formulation was made, prior to any storage of the cream formulation containing the liposome embedded with cardiolipin, methylgentisate, and l-carnosine. FIG. 6(b) is a TEM picture (photograph) of the same standard cream formulation containing the liposome embedded with cardiolipin, methylgentisate, and l-carnosine as in FIG. 6(a) but FIG. 6(b) was taken after the cream formulation was stored for 1 month at 50° C.

DETAILED DESCRIPTION

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular examples only, and is not intended to limit the scope of the present invention, which will be limited only by the claims.

The present invention is based on the surprising discovery that the unique combination of a liposome embedded with cardiolipin and at least one antioxidant improves, maintains, or restores mitochondrial function and/or repairs mitochondrial membranes when administered, for example when topically applied. In one example, the liposome of the present invention is, for example, primarily composed of phosphatidylcholine; the cardiolipin is, for example, one of tetraoleoyl-cardiolipin, tetrapalmitoleoyl-cardiolipin, or tetramyristoyl-cardiolipin; and the antioxidant is, for example, one or more of methylgentisate and l-carnosine.

In addition, the unique composition of the present invention has the surprising advantage of being stable and resistant to oxidative damage, degradation or instability when stored at approximately room temperature or higher. For example, as discussed below in Example 3, a composition of the present invention comprising a liposome primarily composed of phosphatidylcholine and embedded with tetraoleoyl-cardiolipin, methygentisate, and l-carnosine demonstrated significant stability under storage conditions of 50° C. for at least one month.

It is believed that in the present invention the at least one antioxidant stabilizes the cardiolipin until the cardiolipin is delivered to a cell, for example by topical administration of a composition comprising the liposome of the present invention. In one example, the at least one antioxidant stabilizing the cardiolipin is methylgentisate, a powerful antioxidant that protects the cardiolipin from oxidation. Further, by the nature of liposomal delivery technology, the liposome contains a water interior. See, e.g. FIG. 3. To avoid oxidation of cardiolipin from within the liposome, the present invention may comprise a second antioxidant, for example, l-carnosine, which is a powerful peptide based water soluble antioxidant.

Improved cellular function is accomplished by the composition of the present invention because the invention comprises both an antioxidant, for example, l-carnosine, to protect the cell from oxidative damage, and a cardiolipin, for example, tetraoleoyl-cardiolipin, to improve, maintain or restore mitochondrial function, and/or to repair mitochondrial membranes. Supporting evidence for improved, maintained, or restored functional activity of the mitochondria is provided, for example, through in vitro test data. For example, the procedure discussed in Example 2 indicates that administration of a composition of the present invention comprising a liposome primarily composed of phosphatidylcholine and embedded with tetraoleoyl-cardiolipin, methyl gentisate, and l-carnosine resulted in significantly higher levels of ATP production than any of the components alone.

Mitochondria

Mitochondria, present in all cells at varying amounts dependent on the metabolic activity of the cell, are an intended target of the compositions of the present invention. Indeed, the compositions of the present invention are designed to deliver cardiolipin to an integral structure of the mitochondria, the mitochondrial membrane.

Mitochondria are rod-shaped organelles that can be considered the power generators of the cell, converting oxygen and nutrients into adenosine triphosphate (ATP). ATP is the chemical energy "currency" of the cell that powers the cell's metabolic activities. The number of mitochondria in any given cell depends almost entirely on the metabolic activity of that cell. Mitochondria are quite flexible and time-lapse studies of living cells have demonstrated that mitochondria change shape rapidly and move about in the cell almost constantly. Mitochondrial movements appear to be linked in some way to the microtubules present in the cells, and mitochondria probably are transported along the network with motor proteins. Consequently, mitochondria may be organized into lengthy traveling chains, packed tightly into relatively stable groups, or appear in many other formations based upon the particular needs of the cell and the characteristics of its microtubular network.

Mitochondria have elaborate structures that are critical to the functioning of the organelle. Two specialized membranes encircle each mitochondrion present in a cell, dividing the organelle into a narrow intermembrane space and a much larger internal matrix, each of which contains highly specialized proteins. The outer membrane of a mitochondrion contains many channels formed by the protein porin and acts like a sieve, filtering out molecules that are too big. Similarly, the inner membrane, which is highly convoluted so that a large number of infoldings called cristae are formed, also allows only certain molecules to pass through it and is much more selective than the outer membrane. To make certain that only those materials essential to the matrix are allowed into it, the inner membrane utilizes a group of transport proteins that will only transport the correct molecules. Together, the various compartments of a mitochondrion are able to work in harmony to generate ATP in a complex multi-step process.

Specifically, ATP is produced via a complex chain of reactions by passing electrons through 4 complexes and driving a proton concentration buildup, enabling the proton motive force. The four complexes are NADH dehydrogenase, succinate dehydrogenase, $bc_1$, complex, and cytochrome c oxidase. The electron transport and associated oxidative phosphorylation take place on the inner mitochondrial membrane which contains approximately 75% protein and 20% cardiolipin. Integral to functionality is the quarternary structure formed between the inner membrane lipid, cardiolipin, and the proteins comprising the complexes and transport carriers. Examples are cytochrome c oxidase and the ATP/ADP carrier which contain tightly bound cardiolipin, critical for structure and function as reported by Mileykovskaya et al. See Mileykovskaya et al., "Cardiolipin in Energy Transducing Membranes." *Biochemistry (Mosc).* 2005. 70(2):154-8 the entire contents of which are hereby incorporated by reference. In addition, Gorbenko et al., describe the interaction between cytochrome c and cardiolipin in detail. See Gorbenko et al., "Cytochrome c Interaction with Cardiolipin/Phosphatidylcholine Model Membranes: Effect of Cardiolipin on Protonation." *Biophys J.* 2006. 90(11):4093-103, the entire contents of which are hereby incorporated by reference. See also Petrosillo et al., "Role of Reactive Oxygen Species and Cardiolipin in the Release of Cytochrome c from Mitochondria." *FASEB J.* 2003. 17:2202-2208, the entire contents of which are hereby incorporated by reference. Furthermore, a pivotal relationship has been shown by Paradies et al., to exist between cardiolipin and complex III of the electron transport mechanism. See Paradies et al., "Reactive oxygen species generated by the mitochondrial respiratory chain affect the complex III activity via cardiolipin peroxidation in beef-heart submitochondrial particles." *Mitochondrion* 2001. 1:151-159, the entire contents of which are hereby incorporated by reference. See also Paradies et al., "Reactive oxygen species affect mitochondrial electron transport complex I activity through oxidative cardiolipin damage." *Gene.* 2002. 286:135-141, the entire contents of which are hereby incorporated by reference.

Mitochondria play a crucial role in apoptosis induction. Release of cytochrome c from mitochondria appears to be a central event in the induction of the apoptosis cascade that ultimately leads to programmed cell death. Nevertheless, the mechanism underlying cytochrome c release from mitochondria that triggers caspase activation appears to be largely mediated by ROS. In addition, it has been shown that cytochrome c release from mitochondria is preceded by its disassociation from the inner mitochondrial membrane. Cytochrome c is bound to the outer surface of the inner membrane phospholipids, primarily to cardiolipin molecules. The binding of cytochrome c to cardiolipin has been studied extensively and some molecular aspects of the interaction have been elucidated. Cardiolipin is rich in unsaturated fatty acids, which appear to be essential for its interaction with cytochrome c in order to anchor the protein to the membrane. It would be expected that oxidative damage to cardiolipin by ROS may disturb the interaction of cytochrome c with this phospholipid at the level of the inner mitochondrial membrane, and that this, in turn, would induce the dissociation of cytochrome c from the membrane, enabling its release into the extramitochondrial space. Accordingly, a loss of molecular interaction between cytochrome c and cardiolipin due to the lipid peroxidation has been reported. In addition, it has been found that changes in cardiolipin content, due to oxidative damage or to alteration in its biosynthetic path, trigger the release of cytochrome c from mitochondria during the apoptotic process.

Cardiolipin

Cardiolipin is embedded in the liposome of the present invention for delivery to mitochondria. Cardiolipin is found only in membranes of bacteria and of mitochondria. This unique and limited location of cardiolipin in mitochondrial membranes indicates that the liposomes of the present invention target, and/or the cardiolipin embedded in the liposomes will target, the mitochondrial membrane.

Further, as discussed above, cardiolipin is a prominent component of the mitochondrial inner membrane and contributes to the regulation of multiple discrete mitochondrial functions. Indeed, as cardiolipin is the specific lipid component of mitochondria, its biological function in this organelle is clearly crucial. For example, cardiolipin is at least in part responsible for maintaining membrane fluidity. Indeed, as mitochondria lose cardiolipin, they become more rigid, lose functionality and eventually cause cell death. Thus, an added advantage of a composition of the present invention is that delivery of cardiolipin to the mitochondria and the mitochondrial membrane will aid in maintaining, restoring, or repairing mitochondria and/or mitochondrial membrane fluidity.

As discussed above, cardiolipin is located mainly on the inner membrane of mitochondria, where it interacts with a large number of mitochondrial proteins. This interaction affects functional activation of certain enzymes, especially those involved in oxidative phosphorylation. All the mitochondrial protein complexes involved in oxidative phosphorylation contain cardiolipin molecules integrated into their quaternary structure, where they are essential components of the interface between the complex and its environment or between subunits within the complex.

Mitochondrial cardiolipin molecules are a target of oxygen free radical attack because of their high content of unsaturated fatty acids and their location in the inner mitochondrial membrane near the site of ROS production. Removal of cardiolipin from the mitochondrial membrane leads to break-up of the complex and loss of functionality. For example, cardiolipin plays a crucial role in the cytochrome bc1 complex, a membrane protein complex of the respiratory chain that couples electron transfer between ubiquinol and cytochrome c to the translocation of protons across the lipid bilayer. Specifically, one cardiolipin molecule is bound close to the site of ubiquinone reduction and is believed to ensure the stability of the catalytic site as well as being involved in proton uptake.

Cardiolipin is a phospholipid of unusual structure and is particularly rich in unsaturated fatty acids. Typically, linoleic acid represents at least 85% of the unsaturated fatty acids present in cardiolipin. Thus, in one example of the present invention, cardiolipin composed of approximately 85% lineolic acid is embedded in a liposome, for example in the phospholipid bilayer of the liposome. In another example of the present invention, tetraoleoyl-cardiolipin is embedded in the liposome. Tetraoleoyl-cardiolipin is composed of four oleic acid constituents (C18:1, tetraoleoyl-cardiolipin), which are less susceptible to oxidative damage and break down than lineolic acid cardiolipins. In other examples, the cardiolipin of the present invention may be tetrapalmitoleoyl-cardiolipin, tetramyristoyl-cardiolipin, or seed oil derived cardiolipin. Other examples of cardiolipin that can be used in compositions and methods of the present invention are available, for example, from Avanti® Polar Lipids, Inc. (Alabaster, Ala.). Examples of cardiolipin available from Avanti® Polar Lipids, Inc. include the following: 1,1',2,2'-Tetramyristoyl Cardiolipin (Ammonium Salt) (Prod. No. 770332); 1,1',2,2'-Tetramyristoyl Cardiolipin (Sodium Salt) (Prod. No. 750332 or 710335); 1,1'-Oleoyl-2,2'-(12-biotinyl(aminododecanoyl)) Cardiolipin (Ammonium Salt) (Prod. No. 860564); Cardiolipin (*E. Coli*, Disodium Salt) (Prod. No. 841199); Cardiolipin (Heart, Bovine-Disodium Salt) (Prod. No. 770012); Cardiolipin (Heart, Bovine-Disodium Salt) (Prod. No. 840012); Cardiolipin, Hydrogenated (Heart, Bovine-Disodium Salt) (Prod. No. 830057); Dilysocardiolipin (Heart, Bovine-Disodium Salt) (Prod. No. 850082); Dilysocardiolipin (Heart-Sodium Salt); Heart Cardiolipin Hydrogenated; Lysocardiolipin; Monolysocardiolipin (Heart, Bovine-Disodium Salt) (Prod. No. 850081); and Monolysocardiolipin (Heart-Sodium Salt).

In a further example, the cardiolipin embedded in the liposome may be diphosphatidylglycerol or more precisely 1,3-bis(sn-3'-phosphatidyl)-sn-glycerol. Generally all forms of cardiolipin have a dimeric structure, having four acyl groups and potentially carry two negative charges. See e.g. FIG. 2. Even with four identical acyl residues, cardiolipin has two chemically distinct phosphatidyl moieties, as two chiral centers exist, one in each outer glycerol group. These could give rise to diastereomers, although natural diphosphatidylglycerol has the R/R configuration. In consequence, the two phosphate groups have different chemical environments. They are designated 1'-phosphate and 3'-phosphate with respect to the central glycerol. Each form of cardiolipin contains one acidic proton, but they have very different levels of acidity, e.g. $pK1=2.8$ and $pK2>7.5$. The weak acidity of the second phosphate is believed to be a result of formation of a stable intramolecular hydrogen bond with the central 2'-hydroxyl group. In effect, under normal physiological conditions, the cardiolipin molecule may carry only one negative charge. Further, models of cardiolipin show that its phosphates can form a tight bicyclic structure if a proton is trapped forming an acid-anion, giving an especially compact structure.

In animal tissues, cardiolipin is believed to be an important cofactor for cholesterol translocation from the outer to the inner mitochondrial membrane, and in steroidogenic tissues, it activates mitochondrial cholesterol side chain cleavage and is a potent stimulator of steroidogenesis. Cardiolipin may also have a specific role in the import of proteins into mitochondria. It binds in a highly specific way to the DNA in chromatin, and indeed all cardiolipin present in chromatin is bound to DNA, where both have a common 'interphosphate' structural motive. Thus cardiolipin appears to have a functional role in the regulation of gene expression. For example, Barth syndrome, a human disease state (cardiomyopathy) linked to the X-chromosome, is associated with marked abnormalities in the fatty acid composition of cardiolipin, i.e. a decrease in tetra-linoleoyl molecular species, and an accumulation of monolysocardiolipin.

Antioxidants

According to the present invention, at least one antioxidant is embedded with the cardiolipin in a liposome. The antioxidant may, for example, be embedded in the phospholipid bilayer of the liposome, in the aqueous center of the liposome, or both. As explained above, the antioxidant included in a composition of the present invention may function by protecting the cardiolipin from oxidative damage or degradation resulting either from the aqueous center of the liposome or from ROS outside the liposome. Indeed, one major action of antioxidants in cells is to prevent damage due to the action of ROS. Reactive oxygen species include hydrogen peroxide ($H_2O_2$), the superoxide anion ($O_2^-$), and free radicals such as the hydroxyl radical ($OH^-$). These molecules are unstable and highly reactive, and can damage cells by chemical chain reactions such as lipid peroxidation.

There are many antioxidants that may be incorporated in the compositions of the present invention. For example, an antioxidant embedded in a liposome of the present invention might be water-soluble and thus embedded in the aqueous center of the liposome. In another example, an antioxidant embedded in a liposome might be lipid soluble and thus embedded in the lipid bilayer of the liposome. In a further example, an antioxidant embedded in a liposome of the present invention might be a singlet-oxygen scavenger. In another example, the antioxidant may be both water soluble and a singlet-oxygen scavenger or both lipid soluble and a singlet-oxygen scavenger. In a further example, more than one antioxidant might be embedded in the liposome of the present invention. For example, one or more of the following antioxidants might be embedded in the liposome of the present invention: methylgentisate, l-carnosine, butylated hydroxytoluene (BHT), tert-butylhydroquinone (TBHQ), or some combination thereof.

In one example, methylgentisate is used as an antioxidant in the present invention because methylgentisate is lipid soluble and has the ability to stabilize cardiolipin. Although Example 1 discussed below illustrates that methylgentisate did not exhibit significant protection from oxidative stress, methylgentisate has a high oxygen radical absorbency capacity ("ORAC") (25,605 µmol Teq/g), which indicates it is a strong antioxidant. It is possible then to select an antioxidant for use in the present invention based on its ORAC value, for example by selecting antioxidants with high ORAC values. Thus, in one example, methylgentisate is selected for use in the invention because of its high ORAC value. In such an example, the present invention is comprised of a liposome having cardiolipin and methylgentisate embedded, for example, in its phospholipid bilayer.

In another example, l-carnosine is used as an antioxidant in the present invention because it is water soluble and has the ability to protect cardiolipin from oxidative damage due to the aqueous center of the liposome. Thus, in one example, the aqueous center of the liposome contains l-carnosine. In a further example, the phospholipid bilayer of the liposome is embedded with cardiolipin and methylgentisate and the aqueous center of the liposome contains l-carnosine.

In another example, an antioxidant embedded in a liposome of the present invention might be an antioxidant found in mitochondria, such as for example, glutathione. It has been shown that when glutathione is artificially depleted from cells, oxidative damage increases. The level of glutathione in mitochondria might be even more important than the level of glutathione in the rest of the cell. Mitochondrial glutathione levels diminish more with age than do the levels in the rest of the cell. This decline seems to make mitochondria more susceptible to oxidative damage.

Ascorbic acid (i.e. vitamin C) and vitamin E (i.e. tocopherol) are other examples of antioxidants that might be embedded in a liposome of the present invention along with cardiolipin. It should be appreciated that there are numerous other antioxidants that might be embedded in a liposome of the present invention.

Liposomes

According to the present invention, cardiolipin, perhaps with antioxidants, is delivered to the mitochondria using a liposome. Liposomes are known to be efficient drug delivery systems for topical applications in cosmetic and dermatological products. In particular, a liposome is a spherical vesicle with a membrane composed of a phospholipid bilayer. Liposomes can be composed of a variety of phospholipids including naturally-derived phospholipids with mixed lipid chains such as egg phosphatidylethanolamine, or of pure components like DOPE (dioleolylphosphatidylethanolamine). Liposomes typically are small in size, falling in the range of about 25 to 1000 nm. Liposomes are closed structures composed of a phospholipid bilayer and are capable of encapsulating water-soluble, hydrophilic molecules in their aqueous core and oil-soluble, hydrophobic molecules in the hydrophobic region of the bilayer. FIG. 3 illustrates the general structure of a liposome. Generally, a liposome may be neutral, negative or positive. For example, a positive liposome may be formed from a solution containing phosphatidylcholine, cholesterol, cardiolipin and phosphatidyl serine. Liposomes can be a mixture of multilamellar vesicles and unilamellar vesicles.

The lipid bilayer of a liposome can fuse with other bilayers, for example cellular and/or mitochondrial membranes, thus delivering the liposome contents. In one example then, the present invention achieves improvement in, maintenance, restoration, or repair of mitochondria and/or mitochondrial membranes by fusing with a mitochondrial membrane and delivering the embedded cardiolipin to the mitochondria.

As explained above, liposomes are comprised of phospholipids. Phospholipid molecules have a "headgroup" which is hydrophilic in nature and a hydrophobic "tail" consisting of two acyl chains. Aqueous solubility of a phospholipid depends on both the length of the hydrophobic tail and the affinity of the headgroup to water. For example, pure lipids with each acyl chain containing 14 or more carbons in the form of a straight chain (unbranched) with saturated C-C are water insoluble. Generally, as the acyl chain-length of the lipids increases, the critical micelle concentration decreases rapidly.

A liposome of the present invention may be primarily comprised of lipids present in a cellular membrane, including phospholipids, ceramides, sphingolipids, cholesterol, and triglycerides, or other lipids such as phytosterols from plants. In one example, a liposome used in the present invention may be composed primarily of phosphatidylcholine (or phosphatidyl choline). Phosphatidylcholine is a phospholipid that is a major constituent of cell membranes. Phosphatidylcholine is also known as 1,2-dihexadecanoyl-sn-glycero-3-phosphocholine, PtdCho and lecithin. Unsaturated phosphatidylcholine contains choline, omega-6 unsaturated fatty acid (e.g. linoleic acid), omega-3 fatty acids (e.g. gamma-linolenic acid) and has a low level (or absence) of residual glycerides. FIG. 4 shows the chemical structure of phosphatidylcholine. Phosphatidylcholine is important for normal cellular membrane composition and repair.

Specifically, phosphatidylcholine's role in the maintenance of cell-membrane integrity is vital to all of the basic biological processes, including information flow occurring within cells from DNA to RNA to proteins, formation of cellular energy, and intracellular communication or signal transduction. Phosphatidylcholine, particularly phosphatidylcholine rich in polyunsaturated fatty acids, has a marked fluidizing effect on cellular membranes. Decreased cell-membrane fluidization and breakdown of cell-membrane integrity, as well as impairment of cell-membrane repair mechanisms, are associated with a number of disorders, including liver disease, neurological diseases, various cancers and cell death.

Therefore, an added advantage of one example of a composition of the present invention, specifically where the liposome is primarily composed of phosphatidylcholine, is that the liposome may provide additional phosphatidylcholine to cellular and mitochondrial membranes.

Advances in liposome research have enabled liposomes to avoid detection by the body's immune system, specifically, the cells of reticuloendothelial system (RES). Such liposomes are known as "stealth liposomes", and are constructed with PEG (Polyethylene Glycol) as coating. The PEG coating, which is inert in the body, allows for longer circulatory life for the drug delivery mechanism. Thus, a composition of the present invention may be a liposome primarily composed of phosphatidylcholine and embedded with cardiolipin, for example tetraoleoyl-cardiolipin, and at least one antioxidant, for example methylgentisate and/or l-carnosine, and may additionally comprise a PEG "stealth" coating. In addition to a PEG coating, a stealth liposome of the present invention may also have a ligand attached that enables binding to the targeted site of delivery.

In skin care or cosmetic products, liposomes can be formulated in an appropriate matrix such as serums, lotions, gels, or creams. Preferably, the liposomes of the present invention are not prepared in the presence of surfactants. Indeed, in producing the liposomes of the present invention, those of skill in the art will appreciate that the major destabilizing factors for liposomes include surfactants, temperature, pH, and lipid peroxidation. Thus, due care should be exercised to minimize the adverse effects from these.

It should be appreciated that liposomes of the present invention may be manufactured using a variety of techniques and/or obtained from a variety of sources. For example, the liposomes of the present invention may be manufactured using microfluidization techniques, sonication of lipids in water, or formation of a micelle in an emulsion using an emulsifier, such as lecithin. In other examples, liposomes of the present invention may be obtained from Centerchem, Inc., (Norwalk, Conn.) or Lipotech (Spain).

One advantage of manufacturing liposomes of the present invention using the microfluidization technique is the capability to continuously mass produce liposomes. The microfluidization technique does not require any organic solvents to dissolve the lipids; and high concentrations of lipids in aqueous phase can be used with this technique. As a result, microfluidization is highly applicable for use in cosmetics applications such as the present invention.

More specifically, the microfluidization technique involves introduction of slurry-like concentrated lipid/water dispersions in a micro fluidizer which pumps the dispersions at a very high pressure (10,000 to 20,000 psi) through filters of 1-5 µm pore size. The fluid moving at a very high velocity is split into two streams by forcing it through two defined micro channels. The two streams are then made to collide together at right-angles at very high velocity. The tremendous energy imparted by the high pressure and high velocity causes the lipids to self-assemble into liposomes. The fluid collected at the end is re-passed until a homogeneous-looking dispersion is obtained.

As mentioned above, liposomes also can be created by sonicating phospholipids in water. Low shear rates create multilamellar liposomes, which have many layers like an onion. Continued high-shear sonication tends to form smaller unilamellar liposomes. In this technique, the liposome contents may be the same as the contents of the aqueous phase.

Table I (below) shows some examples of liposomes including their sizes, general methods of preparation, corresponding approximate encapsulation volume, encapsulation efficiency, and calculated number of POPC (1-palmitoyl,2-oleoyl phosphatidylcholine) molecules. The actual captured volume or encapsulation efficiency varies depending on the method of preparation of liposomes, type of the liquid, and the active itself. The type and amount of the payload influences the stability of the liposome. The encapsulation efficiency of oil-soluble molecules is nearly 100% because these molecules, for example cardiolipin, reside in the hydrophobic region of the bilayer. The last column on Table I show the calculated number of POPC molecules per POPC liposome of specific size. Table I also illustrates the main thermal phase transition temperature ($T_m$), which is important parameter for choosing the type of lipid employed for the formation of liposomes. It also is useful for determining proper storage conditions of the liposomes.

TABLE I

Methods of Preparation, Characteristics and Calculated Number of POPC Molecules of Exemplary Liposomes

| Type of Liposome | Method of Preparation | Encapsulation volume (µl/µmol lipid) | Encapsulation efficiency, % active encapsulated (water soluble) | Calculated number of POPC molecules in the POPC liposome |
|---|---|---|---|---|
| Small Unilamellar Vesicles (SUV); 20-100 nm | Probe sonication followed by ultracentrifugation to collect vesicles of 20-50 nm Ethanol injection or detergent dialysis followed by extrusion through <100 nm membrane and ultracentrifugation French Press or microfluidization and harvesting by ultracentrifugation | 0.2-0.5 | Up to 15 | SUV: $2.4 \times 10^3$ (20 nm) |
| Large Unilamellar Vesicles (LUV); 100-1000 nm | Ethanol injection or detergent dialysis followed by extrusion French Press or microfluidization | 2-7 | Up to 50 | LUV: $8.1 \times 10^4$ (100 nm), $3.4 \times 10^5$ (200 nm) |
| Multilamellar Large Vesicles (MLV); 100-1000 nm | Hydration of dry lipid film followed by 3-10 freeze-thaw (thawing to >$T_m$) cycles Dehydration-Rehydration Vesicles (DRV): liposomes are stored freeze dried, rehydrated when required | 2.5-6 | Up to 60 | MLV: $7.2 \times 10^7$ (1 µm w/10 layers), $3.2 \times 10^8$ (2 µm w/10 layers) |

TABLE I-continued

Methods of Preparation, Characteristics and Calculated Number of POPC Molecules of Exemplary Liposomes

| Type of Liposome | Method of Preparation | Encapsulation volume (µl/µmol lipid) | Encapsulation efficiency, % active encapsulated (water soluble) | Calculated number of POPC molecules in the POPC liposome |
|---|---|---|---|---|
| Giant Unilamellar Vesicles (GUV); >1000 nm | Reverse-phase Evaporation Vesicles (REV): lipid is dissolved in organic solvent that is immiscible with water to make an emulsion followed y removal of the organic solvent under vacuum results in vesicles of >1 µm size Interdigitated-Fusion Vesicles (IFV); ethanol is added to SUV prepared using saturated long chain PC like DPPC which leads to the formation of lamellar sheets characterized by interdigitated acyl chains. Upon cycling the temperature (>$T_m$ to <$T_m$) unilamellar vesicles of >1 µm are formed | As high as 720 | Up to 60 | GUV: $3.5 \times 10^6$ (1 µm) $3.5 \times 10^7$ (2 µm) $3.5 \times 10^9$ (20 µm) |

Both hydrophobic and hydrophilic molecules can be embedded into liposomes. If water-soluble molecules are embedded during the process of liposome preparation, it is known as "passive loading." It can be achieved by pre-dissolving the hydrophilic molecule(s) in a buffer that is to be used for hydration of the dry lipid. Any non-embedded molecule can thereafter be removed by dialyzing against the blank buffer, or by passing the dispersion through a Sephadex™ gel column. For most cosmetic and personal care products, removal of non-embedded molecules is not considered critical since there is a high cost associated with such processing, and cosmetic molecules are non-toxic at the levels they are commonly used.

By contrast with the hydrophilic molecules, which are entrapped within the core of the liposome, hydrophobic molecules typically are entrapped in the hydrophobic region of the lipid bilayers. The process involves a partitioning method wherein the hydrophobic molecules are dissolved in a suitable organic solvent, along with the lipid. Thereafter, the solvent is removed by drawing a vacuum, then followed by hydration of the lipid. If the molecule is soluble in ethanol, it can be dissolved along with the lipid in the ethanol; liposomes are then produced by the ethanol injection method. In active loading, also referred to as reverse loading, a pH or ionic gradient is first generated between the inside and outside of the liposomes. "Blank" (empty) liposomes are first prepared in a low pH (citrate buffer, pH=~4). Thereafter, a high pH (pH=~7.4) buffer containing the active (e.g. weak organic acid) is then added to the blank liposome. As a result of pH gradient, actives such as weak acids, partition in the internal core.

Factors that influence efficiency of embedding molecules in the liposome include lipid composition used for liposome preparation, type of liposome(s) (SUV/LUV/MLV), method of liposome preparation, and liposome charge. Buffer strength (buffers of higher strength reduce the amount of resulting encapsulation) and the properties of the molecule to be embedded are also important factors that contribute to the encapsulation efficiency. Both water-soluble payloads (due to interactions with the lipid headgroups), and hydrophobic payloads (due to interactions with the fatty acyl chains of the bilayer membrane) influence the molecular packing of the lipid bilayer. Ultimately, these factors impact the stability of liposomes. A pH of approximately 6.5 is preferred for preparation of liposomes having optimal stability.

Compositions of the Present Invention

Thus, the compositions of the present invention comprise a liposome embedded with cardiolipin and at least one antioxidant and are effective for maintaining, restoring or improving mitochondrial function and/or repairing mitochondrial membranes. It should be appreciated that the compositions of the present invention may comprise additives such as water, castor oil, ethylene glycol monobutyl ether, diethylene glycol monoethyl ether, corn oil, dimethyl sulfoxide, ethylene glycol, isopropanol, soybean oil, glycerin, soluble collagen, or Kaolin.

More specifically, compositions of the present invention may additionally comprise one or more humectants, including but not limited to: dibutyl phthalate; soluble collagen; sorbitol; or sodium 2-pyrrolidone-5-carboxylate. Other examples of humectants that may be used in practicing the present invention can be found in the CTFA Cosmetic Ingredient Handbook, the relevant portions of which are incorporated herein by reference.

Further, compositions of the present invention may additionally comprise one or more emollients including but not limited to: butane-1,3-diol; cetyl palmitate; dimethylpolysiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride;

polyethylene glycol; propane-1,2-diol; triethylene glycol; sesame oil; coconut oil; safflower oil; isoamyl laurate; nonoxynol-9; panthenol; hydrogenated vegetable oil; tocopheryl acetate; tocopheryl linoleate; allantoin; propylene glycol; arachis oil; castor oil; isostearic acid; palmitic acid; isopropyl linoleate; lauryl lactate; myristyl lactate; decyl oleate; or myristyl myristate. Other examples of emollients that may be used in practicing the present invention can be found in the CTFA Cosmetic Ingredient Handbook, the relevant portions of which are incorporated herein by reference.

In further examples, compositions of the present invention may additionally comprise one or more penetration enhancers including but not limited to: pyrrolidones, for example 2-pyrrolidone; alcohols, such as ethanol; alkanols, such as decanol; glycols, such as propylene glycol, dipropylene glycol, butylenes glycol; or terpenes.

The compositions of the present invention may also contain various known and conventional cosmetic adjuvants so long as they do not detrimentally affect the desired mitochondrial maintenance, improvement, restoration, and repair functions provided by the compositions. For example, a composition of the present invention can further include one or more additives or other optional ingredients well known in the art, which can include but are not limited to fillers (e.g., solid, semi-solid, liquid, etc.); carriers; diluents; thickening agents; gelling agents; vitamins, retinoids, and retinols (e.g., vitamin $B_3$, vitamin A, etc.); pigments; fragrances; sunscreens and sunblocks; exfoliants; skin conditioners; moisturizers; ceramides, pseudoceramides, phospholipids, sphingolipids, cholesterol, glucosamine, pharmaceutically acceptable penetrating agents (e.g., n-decylmethyl sulfoxide, lecithin organogels, tyrosine, lysine, etc.); preservatives; antimicrobial agents; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, such as Aloe Vera, cornflower, witch hazel, elderflower, or cucumber and combinations thereof. Other suitable additives and/or adjuncts are described in U.S. Pat. No. 6,184,247, the entire contents of which are incorporated herein by reference.

The compositions of the present invention also can include additional inactive ingredients, including, but not limited to co-solvents, and excipients. Useful co-solvents include alcohols and polyols, polyethylene glycols ethers, amides, esters, other suitable co-solvents, and mixtures thereof. The compositions of the present invention can also include excipients or additives such as sweeteners, flavorants, colorants, antioxidants, preservatives, chelating agents, viscomodulators, tonicifiers, odorants, opacifiers, suspending agents, binders, and mixtures thereof.

Other additives that may be included in compositions of the present invention will be apparent to those of skill in the art and are included within the scope of the present invention.

Modes of Administration

The compositions of the present invention may be orally administered, administered by injection or topically administered. Generally, the compositions of the present invention are administered at least on a daily basis. Administration of the compositions of the invention may continue for any suitable period of time. It should be appreciated that the degree of cosmetic enhancement and degree of maintenance, improvement, restoration or repair of mitochondria will vary directly with the total amount and frequency of composition used.

Useful dosage forms can be prepared by methods and techniques that will be well understood by those of skill in the art and may include the use of additional ingredients in producing appropriate dosage forms. In one example, a formulation of the present invention incorporating the liposome of the present invention embedded with cardiolipin and at least one antioxidant is topically administered at least once a day. In another example, the formulation may be administered twice daily. In a further example, the formulation may be administered three to five times daily. In another example, there is no limit on the amount of the formulation that might be administered daily.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

EXAMPLES

Example 1

Measurement of Protection from Oxidative Stress

The assay described in this experiment measures oxidative stress occurring within the mitochondria. As discussed above, the biochemical reactions used by mitochondria to generate energy yielding ATP molecules also produce highly oxidizing superoxide free radical as a by-product. Using flow cytometry, the below example measures the protection various test samples provide from oxidative stress by monitoring the status of superoxide within mitochondria following treatment with the test materials.

MitoSOX Red mitochondrial superoxide indicator (Invitrogen cat#M36008) is a fluorescent dye that is selectively taken up by mitochondria. Once in the mitochondria, Mito-SOX reacts with superoxide free radical to form a fluorescent product (excitation/emission maxima=510/580 nm) that binds to mitochondrial nucleic acid. A higher fluorescence reading corresponds to a higher level of superoxide free radical being present within the mitochondria.

Cell Culture: One 6 well plate is used per sample. Multiple plates may be prepared simultaneously. Refer to Table II for a plate description. THP-1 monocytes (ATCC cat#TIB-202) are plated at $1.5 \times 10^6$ cells/well in 6 well plates (contained in 2 ml/well RMPI 1640 media supplemented with 10% FBS) and incubated for 1 hour before treating.

TABLE II

| Plate Description | | |
|---|---|---|
| Well | Description | Contents |
| 1 | Positive Control | Load: 2 ml of media with $1.5 \times 10^6$ cells<br>Treatment: 1 ml of 300 uM GMEE<br>Challenge: 1 ml of 5 mM $H_2O_2$ |
| 2 | Negative Control | Load: 2 ml of media with $1.5 \times 10^6$ cells<br>Treatment: 1 ml of media<br>Challenge: 1 ml of 5 mM $H_2O_2$ |
| 3 | Normal Control | Load: 2 ml of media with $1.5 \times 10^6$ cells<br>Treatment: 1 ml of media<br>Challenge: 1 ml of media |
| 4 | Sample Replicate #1 | Load: 2 ml of media with $1.5 \times 10^6$ cells<br>Treatment: 1 ml of 300 µg/ml sample solution<br>Challenge: 1 ml of 5 mM $H_2O_2$ |
| 5 | Sample Replicate #2 | Load: 2 ml of media with $1.5 \times 10^6$ cells<br>Treatment: 1 ml of 300 µg/ml sample solution<br>Challenge: 1 ml of 5 mM $H_2O_2$ |

TABLE II-continued

Plate Description

| Well | Description | Contents |
|---|---|---|
| 6 | Sample Replicate #3 | Load: 2 ml of media with 1.5 × 10⁶ cells<br>Treatment: 1 ml of 300 µg/ml sample solution<br>Challenge: 1 ml of 5 mM $H_2O_2$ |

Treatment: Glutathione monoethylester (GMEE, 100 µM final concentration) is used as a positive control. More specifically, the positive control is prepared by making a 1.2 mM stock solution by dissolving 4 mg glutathione monoethylester in 10 ml media (RMPI 1640 media supplemented with 10% FBS). The positive control working solution (300 µM) is then prepared by adding 2.5 ml of the stock solution to 7.5 ml media. One ml of the positive control working solution is added to 1 well of the plate, giving a final treatment concentration of 100 µM glutathione monoethyl ester.

A negative control and a normal control are prepared by adding 1 ml of media (RMPI 1640 media supplemented with 10% FBS) to designated wells on the plate (1 well per control).

The test sample may be prepared by making a sample stock solution at a concentration of 10 mg/ml by weighing 100 mg test sample into a 15 ml-disposable centrifuge tube and adding 10 ml deionized $H_2O$. In this example, the test samples include: Tetraoleoyl cardiolipin, Tetramyristyl cardiolipin, Neolipin® cardiolipin, l-carnosine, and methylgentisate (one plate for each sample). The sample stock solution is then serially diluted to give a sample working solution of 300 µg/ml. 1 ml of the sample working solution is then added to each of three remaining wells on the plate (triplicate wells), giving a final sample concentration of 100 µg/ml for each sample well.

The plate containing both test sample and control wells is then incubated 3 hours at 37° C., 5% $CO_2$.

Challenge: After incubation for 3 hours, the cells in wells containing the test sample, positive control, and negative control are subjected to oxidative stress by introducing a challenge solution The challenge solution is prepared as follows:

852 µl 8.8 M $H_2O_2$+4.15 ml Media (=1.5 M $H_2O_2$)
1 ml 1.5 M $H_2O_2$+9 ml Media (=150 mM $H_2O_2$)
1 ml 150 mM+30 ml Media (=5 mM $H_2O_2$)

1 ml 5 mM $H_2O_2$ is added to all wells of the plate except for the normal control 1 ml of media (RMPI 1640 media supplemented with 10% FBS) is added to the normal control well. The plate is then incubated 3 hours at 37° C., 5% $CO_2$.

Staining: Following incubation with the challenge, the contents of all wells are transferred to flow cytometry tubes and centrifuged at 100×g for 5 minutes. Media above the cells is removed and cells are then stained by adding 1 ml Mito-SOX (5 µM) to each tube. Specifically, the MitoSOX stain is obtained by dissolving 2 vials of MitoSOX (50 µg per vial, Invitrogen cat #M36008) using 13 µL DMSO per vial to give a solution of 5 mM per vial (mw=760 g/mole). The contents of both vials are transferred to 26 ml media (5 µM). The cells are incubated with the stain for 15 minutes at room temperature in the dark.

Flow Cytometry: Following staining, the samples are analyzed by flow cytometry (e.g. Becton-Dickinson FACS Caliber), using 488 nm excitation laser and FL2 588 nm emission filter. The data are linearized to a curve defined by the responses of the negative and normal controls (0% protection=untreated/challenged negative control, 100% protection=untreated/unchallenged normal control). Under these conditions, the positive control (100 µM glutathione methyl ester) provides 35% protection from oxidative stress.

Results: The results of this experiment are reported below in Table 11. As the results demonstrate, tetraoleoyl-cardiolipin provided significant, that is an average of 97% protection, from oxidative stress.

TABLE III

Protection from Oxidative Stress

| Test Sample: | Protection from Oxidative Stress (% Control) |
|---|---|
| Tetraoleoyl cardiolipin | 97% |
| Tetramyristyl cardiolipin | 52% |
| Neolipin ® cardiolipin | 0% |
| L-carnosine | 61% |
| Methylgentisate | 0% |

Example 2

Measurement of ATP Levels

The level of cellular ATP is a marker of cellular and mitochondrial health. As explained in this example, ATP levels can be monitored using an ATP dependent luciferase that generates light in the presence of ATP. The amount of light generated is directly proportional to the amount of ATP present.

CHO-K1 (Chinese hamster ovary) cells are purchased from ATCC (Manassas, Va.) (cell accession #ATCC CCL 61). Cell cultures are established in 96 well opaque plates with 1×10⁴ cells per well. Following adherence, the cells are transferred to low glucose media (1 g/l) and are incubated overnight. Cells cultured in low glucose media have a reduced ATP content.

Following overnight culture, the cells are exposed to t-butyl-peroxide (1 mM) for 2 hours to induce cellular stress. Peroxide reduces ATP levels lower than glucose alone and mimic a damaged cell state. Following peroxide exposure, fresh low glucose media is added back to the cells. Immediately following challenge with peroxide, the cells are exposed to test samples, typically at 1, 10, and 100 mg/ml final concentration. The cells are incubated with the test samples for 4 hours at 37° C. As shown below in Table IV, the test samples used in this example include l-carnosine, DC methylgentisate, empty liposome (cardiolipin only), a liposome obtained from AGI Dermatics, Inc. (Freeport, N.Y.) loaded with tetraoleoyl-cardiolipin, l-carnosine, and methylgentisate, and a liposome obtained from Centerchem, Inc. (Norwalk, Conn.) loaded with tetraoleoyl-cardiolipin, l-carnosine, and methylgentisate.

This assay screens compounds for the ability to restore ATP levels following stressed conditions mimicking a damaged cell state. Therefore, following incubation of the challenged cells with the test samples, the relative cellular ATP levels are measured using the Cell-Titer Glo reagent from Promega (Madison, Wis.) according to the manufacturer's specifications. Briefly, the cells are equilibrated to room temperature at which time the media is flicked out of the wells. The diluted reagent is added to the wells and the plate is incubated at room temperature for 15 minutes. Luminescence is read on a Wallach plate reader.

The mean luminescence of each treatment group is calculated and % untreated control is determined by dividing the mean from each test group by the mean of the untreated control. The untreated control is considered 100% so any result above 100% is considered a net positive increase in cellular ATP levels. The results of this example are reported below in Table IV and at FIG. 5.

TABLE IV

Cellular ATP Production

| Test Ingredient | Dose Administration (μg/ml) | Percent Control ATP Production: |
|---|---|---|
| L-Carnosine | 1 | 109.3% ± 0.0% |
|  | 10 | 97.1% ± 11.3% |
|  | 100 | 99.5% ± 6.2 |
| DC Methylgentisate 1% | 1 | 87.5% ± 6.1% |
|  | 10 | 82.5% ± 4.7% |
|  | 100 | 35.8% ± 12.7% |
| Empty liposome (cardiolipin only) | 1 | 81.7% ± 0.0% |
|  | 10 | 86.9% ± 17.4% |
|  | 100 | 193.6% ± 6.3% |
| Liposome loaded with tetraoleoyl-cardiolipin, methylgentisate, and l-carnosine (Liposome from AGI Dermatics, Inc. (Freeport, NY) | 1 | 150.0% ± 7.4% |
|  | 10 | 183.4% ± 0.9% |
|  | 100 | 189.0% ± 7.1% |
| Liposome loaded with tetraoleoyl-cardiolipin, methylgentisate, and l-carnosine (Liposome from Centerchem, Inc. (Norwalk, CT) | 1 | 150.2% ± 8.7% |
|  | 10 | 152.3% ± 16.2% |
|  | 100 | 185.4% ± 17..0% |

| Test Ingredient | Percent Control ATP Production: |
|---|---|
| High glucose control | 153.0% ± 5.8% |
| Low glucose control | 120.8% ± 33.3% |
| High glucose control with t-butyl | 115.7% ± 6.1% |
| Low glucose control with t-butyl | 100.0% ± 17.0% |

These results illustrate that the loaded liposomes augmented ATP levels in cells exposed to oxidative stress at low concentrations. The empty liposomes, with cardiolipin only, augmented ATP at a high concentration, indicating that the other components loaded into the liposomes were important for the effect of the loaded liposomes at low concentrations. The results also show that the other components had little effect when tested by themselves. These results indicate that the liposomal delivery vehicle aided in getting the cardiolipin and antioxidants into the cells.

Example 3

Liposome Stability

Transmission electron microscopy (TEM) is often used to determine the size and morphological characteristics of liposomes. A commonly used method of sample preparation for obtaining a TEM image is to apply a drop of the liposome suspension into a plastic-coated grid, then negatively stain the material with phosphotungstic acid or ammonium molybdate. The result is a monolayer of liposomes embedded in the negative stain.

More specifically a sample may be prepared for TEM imagery as follows: 1% aqueous agarose (w/v) is poured into plastic Petri dishes and air-dried at room temperature for 10 minutes. Formvar or collodion coated grids are made hydrophilic by glow discharge and the grids are placed on Whatman no. 1 filter paper. One drop of the sample suspension is placed on each grid. When most of the liquid is absorbed at the periphery of the grid by the filter paper, the grids are transferred to the agarose plates for 30 minutes to 1 hour to facilitate salt and liquid diffusion into the agarose.

The unstained grids are viewed and photographed using a Zeiss-902 with ESI. The liposomes should appear as discrete round structures and clumping should not be observed.

This method was used to determine the stability of a liposome of the present invention. TEM pictures were taken to determine the size and structure of a liposome of the present invention in a cream formulation both prior to storage and 1 month after storage. Specifically, the liposome analyzed was composed primarily of phosphatidylcholine and embedded with tetraoleoyl-cardiolipin, methylgentisate and l-carnosine. TEM pictures were taken immediately after adding the liposome(s) to the cream formulation and after 1 month of storage of the liposomes (in the cream formulation) at approximately room temperature (50° C.). The TEM pictures of the liposomes of the present invention obtained before storage and after 1 month of storage are shown at FIG. 6. As these TEM pictures demonstrate, after 1 month of storage the liposomes remained discrete, stable structures having intact membranes.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The invention claimed is:

1. A storage stable composition for improving, maintaining or restoring mitochondrial function comprising a plurality of liposomes, wherein each liposome has a lipid bilayer formed from a phosphatidylcholine and has a cardiolipin selected from the group consisting of tetraoleoyl cardiolipin, tetrapalmitoleoyl cardiolipin, tetramyristoyl cardiolipin or mixtures thereof and methylgentisate embedded in the lipid bilayer and a second antioxidant contained in an aqueous center of the liposome, wherein the composition is stable at temperature from about 10° C. to about 60° C.

2. The composition of claim 1 wherein the second antioxidant is l-carnosine.

3. The composition of claim 2, wherein the composition comprises:
   between approximately 0.01 and approximately 10 percent by weight tetraoleoyl-cardiolipin;
   between approximately 0.01 and approximately 10 percent by weight methylgentisate; and
   between approximately 0.01 and approximately 10 percent by weight l-carnosine.

4. The composition of claim 1, wherein the cardiolipin is tetramyristoyl cardiolipin.

5. The composition of claim 1, wherein the cardiolipin is tetrapalmitoleoyl cardiolipin.

6. The composition of claim 1, wherein the liposome further comprises one or more of the following: cholesterol, cholesterol sulfate, ceramides, phytosterols and sugars.

7. The composition of claim 2, wherein the composition is topically administered as a cream, lotion, gel, tonic, oil-in-water emulsion, water-in-oil emulsion, paste, or spray.

8. The composition of claim 7, wherein the composition further comprises one or more of an emollient, a humectant, a penetration enhancer, a vitamin, a fragrance, a pigment, and a moisturizer.

9. A method of improving, maintaining, or restoring mitochondrial function in a cell comprising administering the composition of claim 2 to the cell.

* * * * *